United States Patent
Nüsser et al.

(10) Patent No.: US 10,926,012 B2
(45) Date of Patent: Feb. 23, 2021

(54) BLOOD PUMP, PREFERABLY FOR ASSISTING A HEART

(71) Applicant: Berlin Heart GmbH, Berlin (DE)

(72) Inventors: Peter Nüsser, Kleinmachnow (DE); Leonid Choub, Berlin (DE); Kurt Graichen, Berlin (DE); Jörg Müller, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 130 days.

(21) Appl. No.: 15/758,797

(22) PCT Filed: Sep. 12, 2016

(86) PCT No.: PCT/EP2016/071403
§ 371 (c)(1),
(2) Date: Mar. 9, 2018

(87) PCT Pub. No.: WO2017/042377
PCT Pub. Date: Mar. 16, 2017

(65) Prior Publication Data
US 2018/0303991 A1    Oct. 25, 2018

(30) Foreign Application Priority Data
Sep. 11, 2015    (EP) ...................................... 15184862

(51) Int. Cl.
*A61M 1/12*    (2006.01)
*A61M 1/10*    (2006.01)

(52) U.S. Cl.
CPC ............ *A61M 1/122* (2014.02); *A61M 1/101* (2013.01); *A61M 1/1015* (2014.02);
(Continued)

(58) Field of Classification Search
CPC .... A61M 1/122; A61M 1/1015; A61M 1/101; A61M 1/1086; A61M 1/1017; A61M 1/1036; A61M 2205/3334
(Continued)

(56) References Cited

U.S. PATENT DOCUMENTS 5,112,200 A * 5/1992 Isaacson ............. F04D 13/0646
                                                      415/900
5,824,070 A  10/1998 Jarvik
(Continued)

FOREIGN PATENT DOCUMENTS

CN       1491323 A       4/2004
EP    2 520 317 A1      11/2012
(Continued)

OTHER PUBLICATIONS

International Search Report with English translation, dated Nov. 9, 2016, pp. 1-5, issued in International Application No. PCT/EP2016/071403, European Patent Office, Rijswijk, Netherlands.
(Continued)

*Primary Examiner* — Erin M Piateski
(74) *Attorney, Agent, or Firm* — Brinks Gilson & Lione (57) ABSTRACT

The present application relates to a blood pump, preferably for assisting a heart, wherein the blood pump comprises a housing with a distal inlet, a proximal inlet, and a mandrel arranged between the inlet and the outlet. A rotor with blading is arranged on the mandrel coaxially and rotatably. The rotor is mounted on the mandrel magnetically in an axial direction. In one embodiment the outlet is situated proximally to a proximal end of the blading of the rotor.

17 Claims, 6 Drawing Sheets

(52) U.S. Cl.
CPC ......... *A61M 1/1086* (2013.01); *A61M 1/1017* (2014.02); *A61M 1/1036* (2014.02); *A61M 2205/3334* (2013.01)

(58) Field of Classification Search
USPC .......................................................... 600/17
See application file for complete search history.

(56) References Cited

U.S. PATENT DOCUMENTS

| | | |
|---|---|---|
| 7,934,909 B2 | 5/2011 | Nuesser et al. |
| 9,987,405 B2 | 6/2018 | Nüsser et al. |
| 2006/0183962 A1* | 8/2006 | Okubo ................ A61M 1/1031 600/16 |
| 2011/0238172 A1* | 9/2011 | Akdis ................. F04D 13/0666 623/3.11 |
| 2012/0095281 A1* | 4/2012 | Reichenbach ...... A61M 25/005 600/16 |
| 2014/0171727 A1* | 6/2014 | Nusser ................. A61M 1/122 600/16 |

FOREIGN PATENT DOCUMENTS

| WO | WO 89/07427 | 8/1989 |
|---|---|---|
| WO | WO 2007/105842 | 9/2007 |

OTHER PUBLICATIONS

Chinese Office Action with English translation, issued in CN Application No. 201680052109.7, dated Mar. 27, 2020, pp. 1-18, China National Intellectual Property Administration, Beijing, CN.

* cited by examiner

BLOOD PUMP, PREFERABLY FOR ASSISTING A HEART

CROSS-REFERENCE TO RELATED APPLICATIONS

This application is a 371 nationalization of international patent application PCT/EP2016/071403 filed Sep. 12, 2016, which claims priority under 35 USC § 119 to European patent application 15184862.9 filed Sep. 11, 2015. The entire contents of each of the above-identified applications are hereby incorporated by reference.

TECHNICAL FIELD

The present application relates to a blood pump.

DETAILED DESCRIPTION

Blood pumps, for example for assisting a heart, are used for example in patients with cardiac insufficiency or vascular weakness. The blood pumps described in this application can be used for example as ventricular assist devices (VADs) in order to assist the left ventricle, the right ventricle, or for both ventricles in the case of a system having two pumps.

For example, US 2014/0322020 describes a VAD having a radial pump. Radial pumps are characterised in that they comprise a rotor with a blading, wherein the blading extends radially from a pump inlet to a pump outlet. The blood transported through the rotor is moved on account of the shape of the rotor and the blading arranged thereon, wherein the conveying operation and the associated blood damage are dependent on the shape of the rotor and the blading arranged thereon.

A further blood pump is presented in US 2006/0024182. Here as well, the pump is a radial pump, in which a motor, which lies proximally of the rotor, applies a torque to the rotor and thus sets it in rotation. The disadvantage of a construction of this kind is that the motor has a plurality of rotating components in addition to the rotor.

The object of the present application is to provide a blood pump which is of simple structure and with which blood can be conveyed with little blood damage.

Here, the blood pump comprises a housing with an inlet arranged upstream (also hereinafter: distal inlet) and an outlet arranged downstream (also hereinafter: proximal outlet) and a mandrel arranged between the inlet and the outlet. Here, the mandrel extends from the end of the pump arranged downstream, in an upstream direction in the interior of the housing between the inlet arranged upstream and the outlet arranged downstream. A rotor with an axis and blading is arranged on the mandrel coaxially and rotatably, wherein the rotor is magnetically mounted on the mandrel in an axial direction. The terms "distally" and "proximally" used hereinafter do not provide any restriction in respect of the position of installation of the pump, and merely describe the arrangement of individual components relative to one another.

Here, the outlet is arranged downstream of an end of the blading that is arranged downstream, or rather the rotor is arranged in the housing in such a way that a blading ends upstream of the outlet arranged downstream.

A blood pump having features of this kind is thus designed such that the rotor firstly conveys the blood between the inlet and proximal outlet with an axial component, wherein the blading ends proximally of the outlet. The blood is then pumped by the inflowing conveyed blood in the direction of the outlet and through the outlet of the pump in the direction of a (blood) vessel.

Since the rotor is mounted magnetically on the mandrel in the axial direction, an active bearing or a passive bearing can be formed axially depending on the field of use of the pump. In the case of an axial, passive magnetic bearing, permanent magnets are arranged both in the rotor and in the pump housing or in the mandrel and are oriented relative to one another in such a way that a movement of the rotor in the direction of the distal pump inlet is prevented on account of rising magnetic forces in the event of a movement of the rotor in the distal direction. For example, the permanent magnets can have a magnetisation parallel to the axis of the mandrel.

With the use of an active axial magnetic bearing, permanent magnets of the rotor interact with a control coil. A flow of current through the control coil changes the magnetic field and can attract or repel the permanent magnets of the rotor. The position of the rotor is determined for example with the aid of a sensor coil, and a possible target distance or a possible target position of the rotor (depending on the working point of the pump) is produced by applying an appropriate current to the control coil. Magnetic bearings have proven to be particularly low-maintenance.

The mandrel can perform a function of radially supporting the rotor. The mandrel for example thus prevents the rotor from assuming arbitrary positions within the housing in the radial direction. In addition, the mandrel in some exemplary embodiments can contain components of a stator for driving the rotor. Additionally or alternatively, permanent magnets, for example in the form of magnetic rings, can be arranged in the mandrel and form part of the magnetic, axial mounting. In other exemplary embodiments, elements of the stator which set the rotor in rotation can also be arranged for example within the housing, so that these stator components radially surround the rotor. In respect of the mandrel, the inlet and the outlet, reference is made for example to document WO 2012/150045, which presents a heart pump with a mandrel on which a rotor is arranged. Here, it should be noted however that in that document the blading does not appear to end distally of the outlet.

Further exemplary embodiments will be described hereinafter and in the drawings.

In one embodiment, the outlet is arranged completely proximally of a proximal end of the blading. This is understood to mean that a positive distance, different from zero, exists between the proximal end of the blading of the rotor and the distal start of the outlet. Based on the pump parameters constituted by rotational speed, rotor size, blading size and the like, the distance can be determined such that blood damage is minimised. In some exemplary embodiments the distance between the outlet and the blading is greater than 0.05 mm, preferably greater than 0.1 mm, 0.5 mm, 1 mm or 3 mm, and less than 10 mm, preferably less than 5 mm. With regard to the determination of the distance between the proximal end of the blading and the proximal outlet, the distance can be measured in some exemplary embodiments between the distal point of the proximal outlet, projected onto the axis of the mandrel or rotor, and the proximal end of the blading, projected onto the axis of the mandrel or rotor. In other exemplary embodiments, the distance can be measured between a distal point of a spiral chamber and the proximal end of the blading, in each case projected onto the axis of the mandrel or rotor. A spiral chamber or tangential chamber can be understood here to mean a region of the housing that adjoins a main body, which for example is cylindrical, and that is shaped in such a way (for example as a screw shape) that a tangential component of the flow rate is enforced upon the blood on account of the housing geometry. Here, the transition from the main body to the volute can run continuously or intermittently, in the sense that a diameter of the main body widens continuously or intermittently to a larger diameter of the spiral chamber.

In a particularly preferred variant the outlet is inclined relative to the axis of the rotor by an angle of more than 45°, preferably between 80° and 100°. In particular, the outlet can comprise a spiral housing (or also: volute), the outlet direction of which deviates substantially by 90° from the axis of the rotor. Here, the outlet can be formed for example as a spiral housing, as is presented for example in WO 2012/150045.

In a further embodiment, the rotor comprises a bushing, in particular a cylinder bushing, wherein the blading is arranged along an outer periphery of the bushing. The cylinder bushing shape of the rotor has the advantages that a cylindrical mandrel can also be used. Here, at least one inner wall of the cylinder bushing is cylindrical. In an optional embodiment an outer wall of the cylinder bushing is also cylindrical, and the blading is arranged on the outer wall. Alternatively or additionally, the inner wall and/or the outer wall can also comprise structures which improve the hydrodynamic behaviour of the rotor, such as channels or grooves. These structures, however, do not change the cylindrical shape of the inner or outer wall, and therefore these have a substantially constant radial distance from an axis of rotation of the rotor. Both the cylinder bushing and a cylindrical mandrel have the advantage that this geometry can be produced relatively easily, and therefore the pumps can be produced economically. In addition, it has been found that the design of the mounting of the motor is simplified by the cylinder bushing. A cylinder bushing also offers the possibility to form a cavity between a cylinder inner wall and a cylinder outer wall, in which cavity permanent magnets for example can be, or are arranged for an axial magnetic bearing.

In a further embodiment a hydrodynamic bearing is located between the bushing and the mandrel. Here, the gap between the surface of the mandrel and an inner circumference of the rotor or the bushing or the cylinder bushing is of such a size and design that blood flowing through the gap stabilises the rotor radially and thus forms a radial bearing. Here, the radial bearing can be formed for example between two substantially parallel surfaces of the rotor or the mandrel, the distance between which is selected in such a way that the blood flowing through forms a sliding surface. In other variants either the surface of the mandrel and/or the inner surface of the rotor can be provided with channels or similar structures in order to form the hydrodynamic bearing. Reference is made for example to WO 2012/150045 with regard to the hydrodynamic bearing.

In a further embodiment the blading is formed as a spiral. Here, a spiral is understood mean a helical structure that is wound for example over a cylinder surface. Here, the rotor can comprise just one spiral or a plurality of spirals. In numerous exemplary embodiments the spiral has a width, considered in cross-section, which is much smaller than the distance between two spirals on the rotor surface. An example of a blading is for example the Archimedes' screw. This means that the width of the surfaces by which the blood is conveyed is greater than the width of the spiral. The liquid is "screwed" so to speak in the direction of the outlet. Reference is made to WO 2012/150045 with regard to the spiral as well.

In a further embodiment, the rotor is formed in such a way that a proximal end of the rotor lies proximally of the proximal end of the blading of the rotor. In other words, the rotor extends further in the proximal direction than the blading. There is thus a proximal portion of the rotor which is not provided with a blading. A rotor of this kind for example enables a very simple embodiment of the mandrel. Here, the mandrel does not need to have any structurings.

In further embodiments, the mandrel comprises a first distal portion for receiving the rotor and a second portion arranged proximally of the first portion, wherein, between the first and second portion, a shoulder forms a stop for a proximal end of the rotor. In this embodiment, the rotor can be provided with a blading as far as its proximal end. On account of the shoulder, which lies distally of the proximal outlet, the blading of the rotor also ends distally of the proximal outlet. On the one hand, a mechanical stop of the rotor is formed by the shoulder, and furthermore a hydrodynamic pressure can be built up in the region of the pump between the shoulder and the rotor, which hydrodynamic pressure prevents the rotor from contacting the shoulder.

In a further embodiment the mandrel has a substantially annular recess, in which the rotor is rotatably mounted. This has the advantage for example that the rotor cannot escape mechanically in the axial direction. A disadvantage, however, is the more complicated assembly of the blood pump. In some variants of the presence of an annular recess, the blading of the rotor is arranged radially outside the recess.

Figure 1:
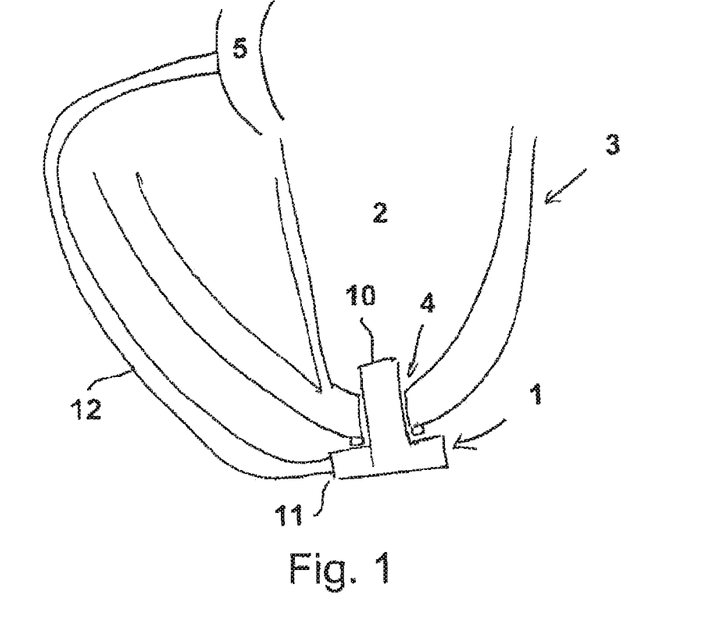
FIG. 1 shows a use of a blood pump as VAD.
Figure 2:
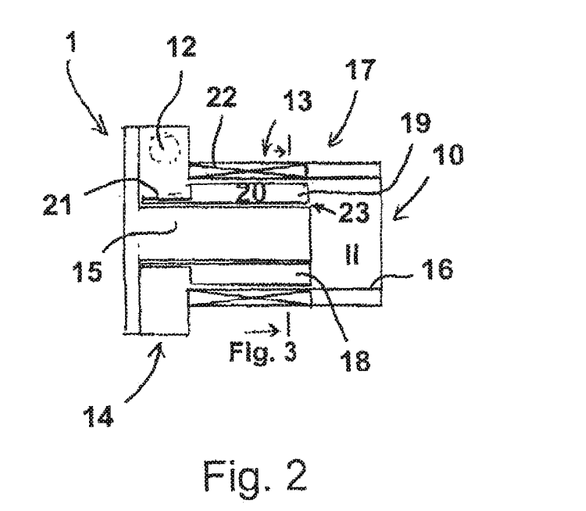
FIG. 2 shows a schematic depiction of a blood pump in longitudinal section.
Figure 3:
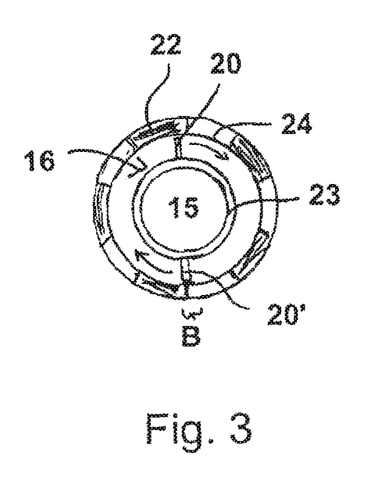
FIG. 3 shows a schematic depiction of the blood pump of FIG. 2 in cross-section.
Figure 4:
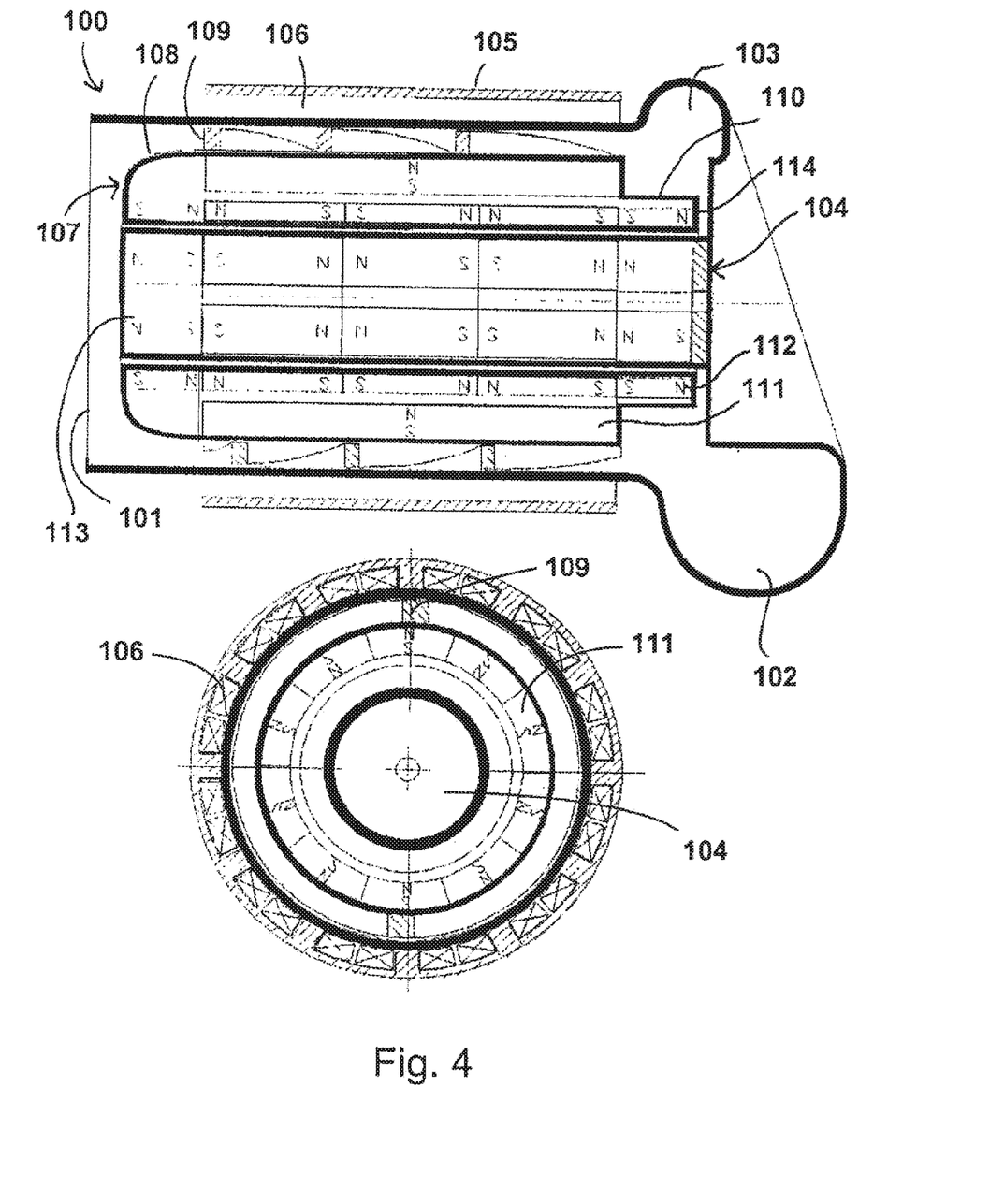
FIG. 4 shows an embodiment of a blood pump according to the application with cylindrical mandrel.
Figure 5:
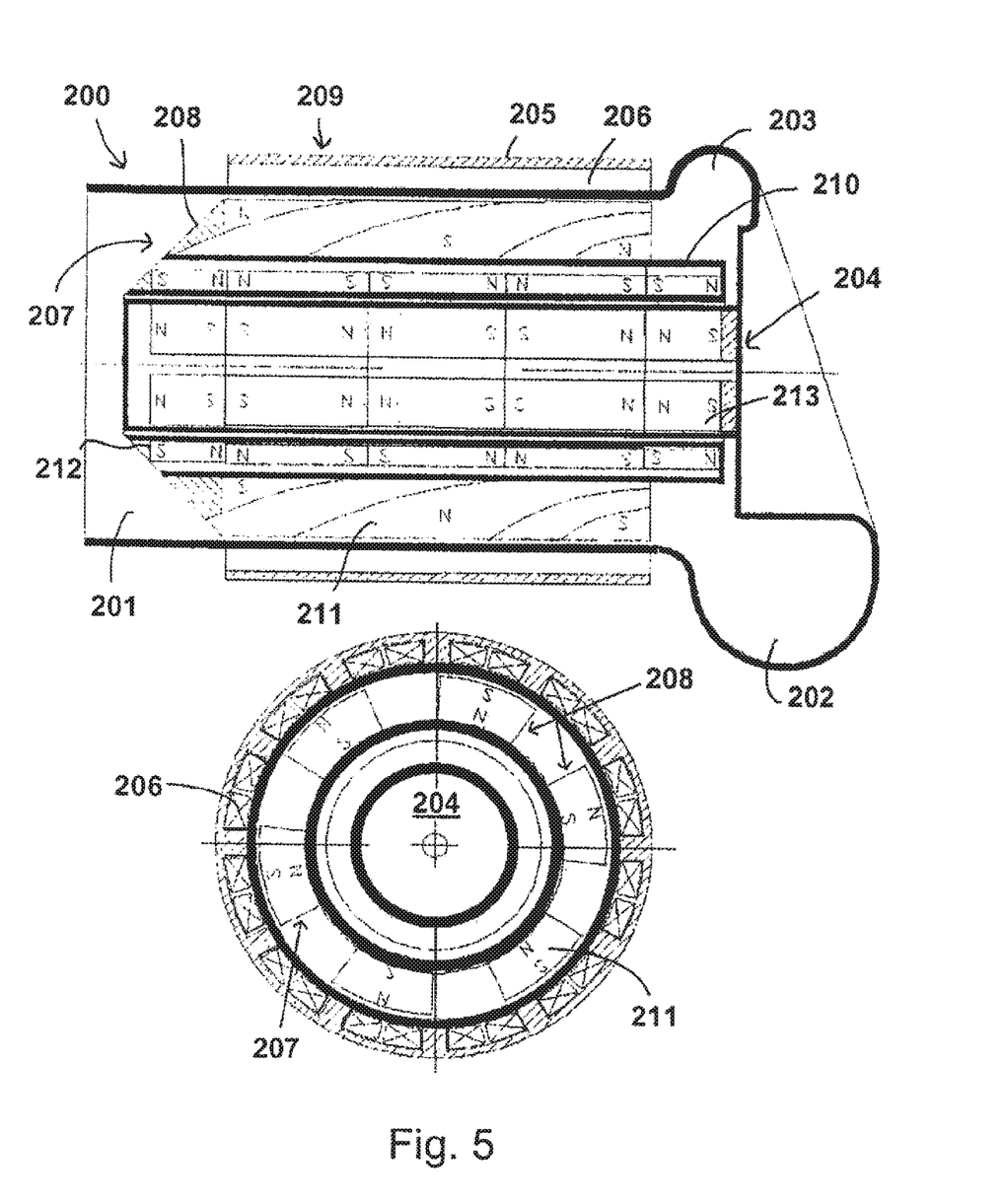
FIG. 5 shows an embodiment of a blood pump according to the application with cylindrical mandrel.
Figure 6:
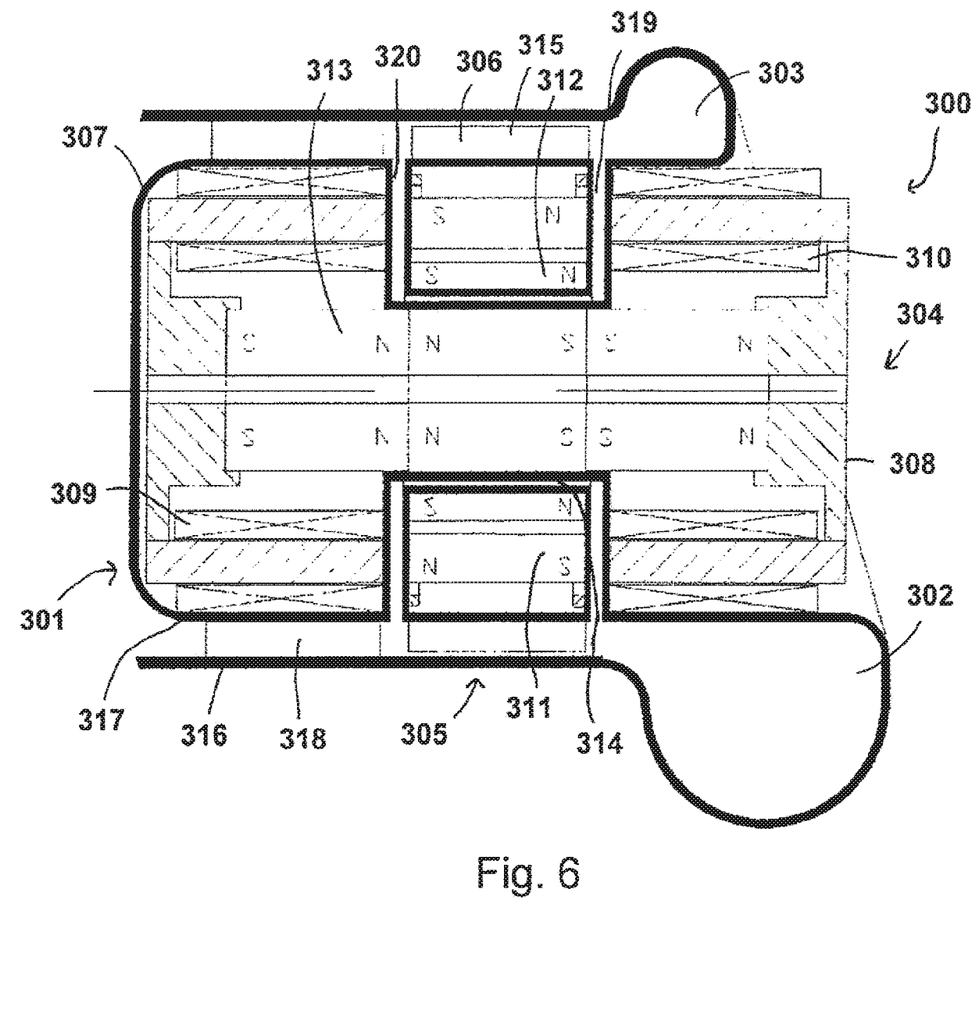
FIG. 6 shows a longitudinal section of an embodiment of a blood pump with an annular recess.
Figure 7:
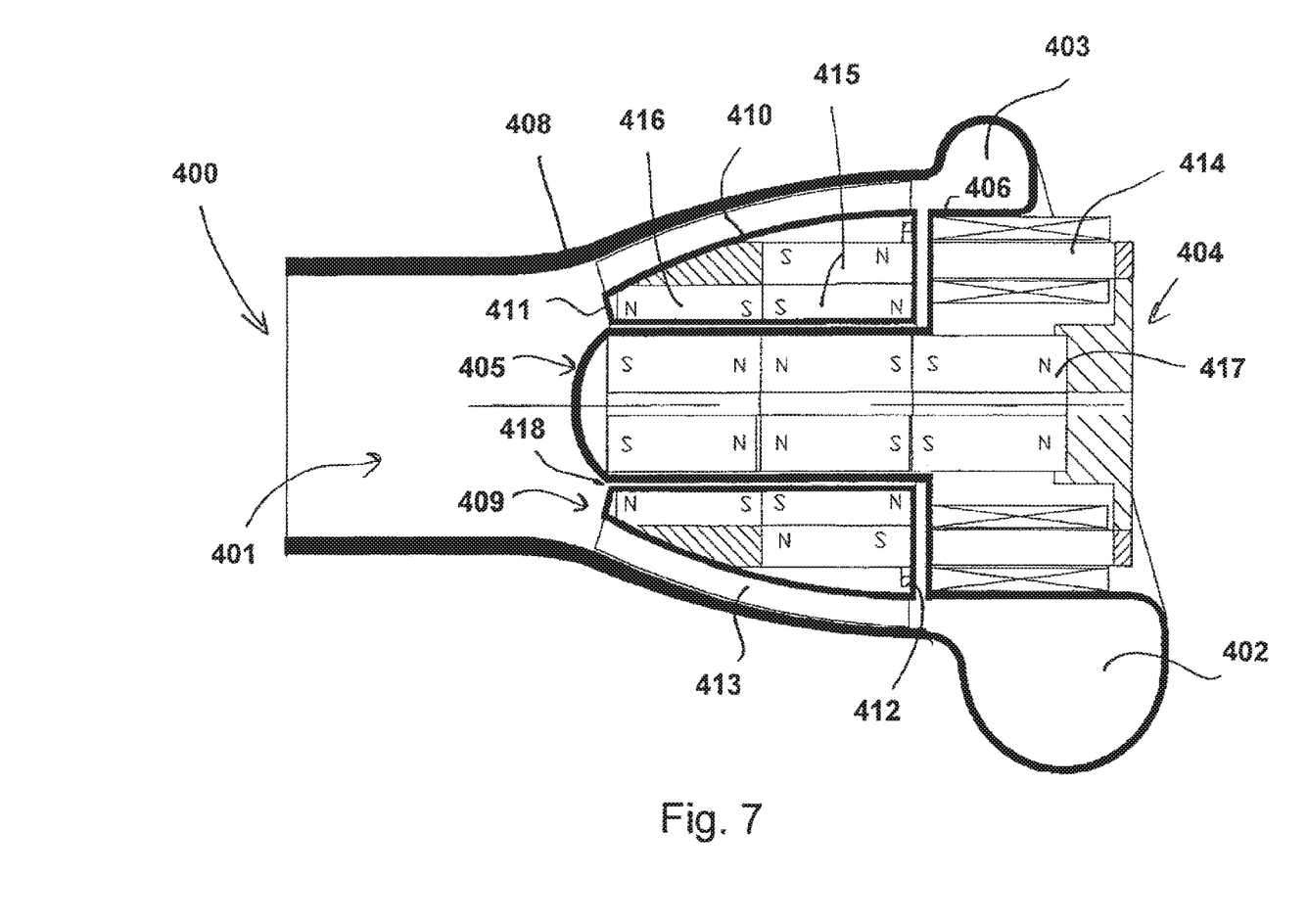
FIG. 7 shows an embodiment of a blood pump with a shoulder arranged on the mandrel.
Figure 8:
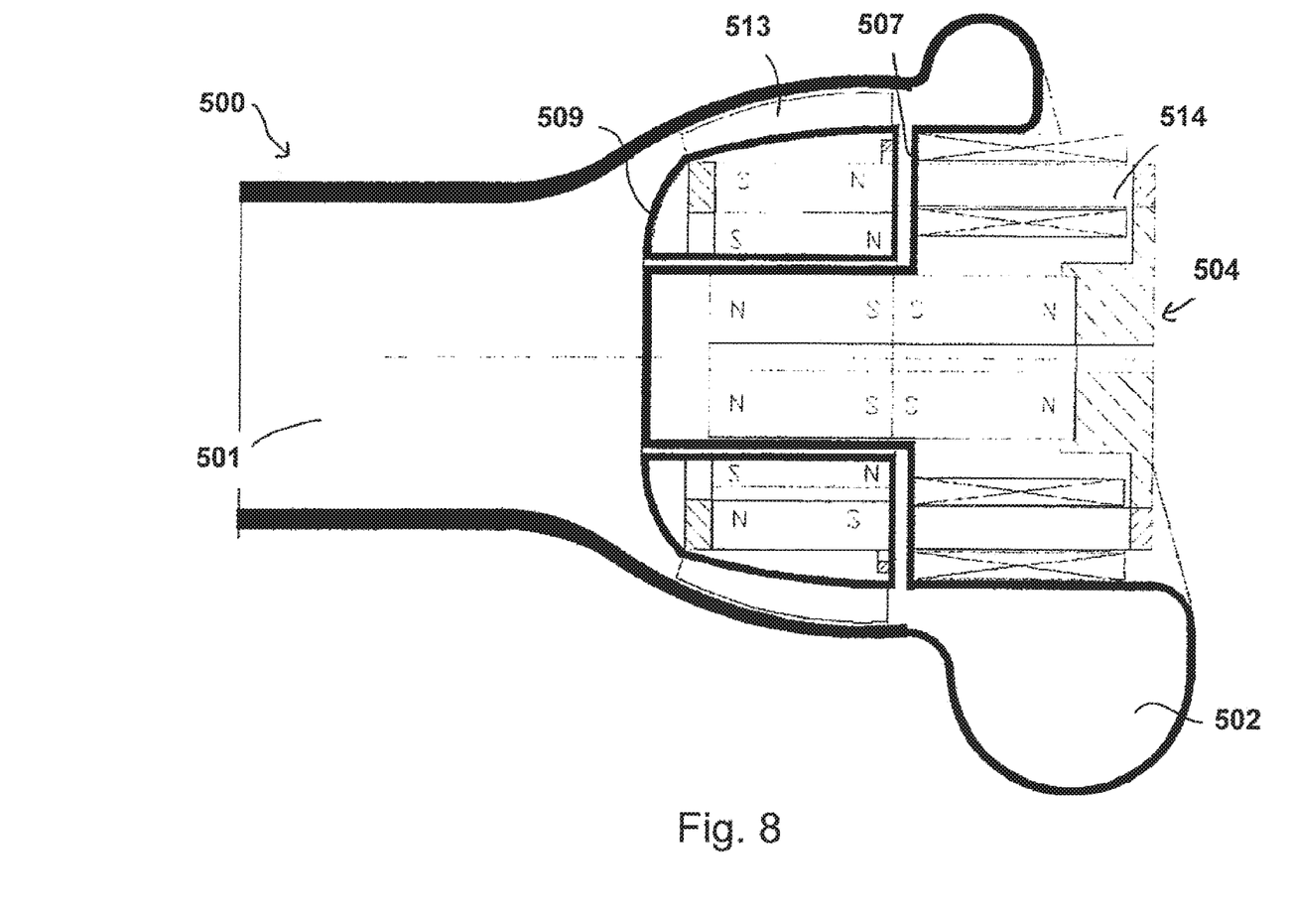
FIG. 8 shows an embodiment of a blood pump with a shoulder arranged on the mandrel.

The subject matter of the application will be described in greater detail on the basis of the elements described in the drawings, in which:

FIG. 1 shows a use of a blood pump as VAD;

FIG. 2 shows a schematic depiction of a blood pump in longitudinal section; FIG. 3 shows a schematic depiction of the blood pump of FIG. 2 in cross-section;

FIG. 4 and FIG. 5 show embodiments of a blood pump according to the application with cylindrical mandrel;

FIG. 6 shows a longitudinal section of an embodiment of a blood pump with an annular recess;

FIG. 7 and FIG. 8 show embodiments of a blood pump with a shoulder arranged on the mandrel.

FIG. 1 shows a blood pump 1, which is arranged in a left ventricle 2 of a heart 3. Here, an inlet 10 protrudes through a hole in the apex 4 of the heart, so that blood is fed through the inlet 10 of the blood pump 1 and can be fed through the proximal outlet 11 via a graft or a cannula 12 to a further vessel, for example an aorta 5. Although the blood pump 1 in the present exemplary embodiment is arranged in the left ventricle 2 and therefore forms an LVAD (left VAD), it can also be designed in other embodiments also as an RVAD (right VAD) or in combination with a further blood pump as a BiVAD (biventricular assist device).

The blood pump 1 comprises further elements, which are not shown here for simplification. For example, the blood pump comprises a control unit, which can be arranged in the pump housing or outside the human or animal body. In addition, the blood pump is connected to a power supply system, so that the pump is provided with sufficient power for operation. The blood pump can also comprise a "driveline", via which control signals can be guided from the pump to the extracorporeal control unit or the power supply can be fed from the extracorporeal supply unit to the blood pump 1.

Although not detailed further in the present application, the blood pump 1 can comprise electronics in its housing. For example, sensor data, which are present in the form of analog signals, can hereby be digitised and thus supplied to the control unit.

In FIG. 2 the exemplary blood pump 1 of FIG. 1 is shown in a longitudinal section. As already described with reference to FIG. 1, the blood pump 1 comprises a distal inlet 10 and a proximal outlet 11. A cavity 12 extends between the inlet 10 and the outlet 11, and more specifically extends between a distal cylindrical portion 13 and a spiral outlet 14 in the region of the outlet 11. A mandrel 15 protrudes into the spiral housing 14 and the distal portion 13 from the proximal end to the distal end. Here, the mandrel is formed in such a way that a gap of sufficient size to fit a rotor 18 onto the mandrel 15 remains between an inner wall 16 of the distal portion of the housing 17 and the mandrel 15. The rotor 18 comprises a distal portion 19 with a blading 20. A proximal portion 21 is also shown, which adjoins the distal portion 19. The proximal portion 21, which protrudes into the spiral chamber 14, here does not have a blading, and therefore the blading 20 ends distally of the proximal outlet 11 and distally of the spiral chamber 14. In the present exemplary embodiment a stator is arranged within a cavity 12 in order to set the rotor in rotation. The stator 22 surrounds the rotor 18 and is arranged in a gap or cavity of the housing.

A radial gap 23 is situated between the rotor 18 and the mandrel 15 and is formed in such a way that a blood film forms in this gap as soon as the rotor is set in motion, and the rotor 18 is supported on this blood film. In this way, the radial gap 23 forms a hydrodynamic bearing. Here, the blood flow direction within the gap 23 is opposite the direction of conveyance of the blood through the pump in some exemplary embodiments.

There is a gap between a radially outer diameter of the rotor 18, in particular a radially outer diameter of the blading 20, and the inner wall 16 of the housing 17, which gap in some exemplary embodiments does not form a hydrodynamic bearing.

The mandrel 15 protrudes into the distal portion 13 of the blood pump 1. At its distal end, the mandrel 15 is formed flat in the present example. In other exemplary embodiments the mandrel can be rounded or formed in a widening manner at its distal end. This can reduce the flow resistance of the blood. A cross-section through the blood pump 1 of FIG. 2 is shown in FIG. 3. The cylinder shape of the mandrel 15 is clearly visible in the cross-section. The radial gap 23 is located between the rotor 18, in particular an inner surface of the rotor 18, and an outer surface of the mandrel 15, said gap being dimensioned in such a way that a blood film is formed in the gap as the rotor 18 rotates and forms a hydrodynamic bearing between the two surfaces.

A blading 20 and a further blading 20' extend from the rotor 18. The bladings 20 and 20' are each a spiral. These surround the rotor 18 in the radial direction in a helical or helix-like manner. It can be clearly seen that the width B of the spiral 20' is much smaller than the distance between the two spirals 20 and 20'. A cavity 24 of the stator 22, which sets the rotor 18 in rotation, is arranged surrounding the rotor externally. Alternatively to an arrangement of the stator 22 in a cavity 24 of the housing, the stator can also be arranged within the mandrel in some exemplary embodiments.

Various embodiments of a pump according to the present application will be described with reference to FIGS. 4 to 8. FIG. 4 shows a cross-section through a blood pump 100 which comprises a distal inlet 101 and a proximal outlet 102. The proximal outlet 102 in this case is the end of a spiral chamber of increasing cross-section, running in a spiralled manner. This can be seen for example on the basis of the smaller cross-section 103. A mandrel 104 extends from the proximal end to the distal end. A cylindrical cavity, which is interrupted merely by the mandrel 104, extends between the inlet 101 and the spiral chamber. A housing 105 is arranged surrounding the cavity, wherein a stator 106 is disposed in the housing. A rotor 107 is fitted onto the mandrel or journal 104. The rotor comprises a distal portion 108 with a spiral 109. The rotor 107 further comprises a proximal portion 110, which does not have a blading and which starts distally of the spiral outlet and extends as far as the proximal end of the rotor. So that the rotor can be set in rotation, it comprises permanent magnets 111, which are radially magnetised. By contrast, the rotor comprises further permanent magnets 112, which have an axial magnetisation. Permanent magnets 113, which are likewise axially oriented, are arranged in the mandrel 104 correspondingly to the axially magnetised permanent magnets 112 and form a passive magnetic axial bearing in conjunction with the permanent magnets 112. The magnetisation of the permanent magnets 112 is oriented opposite the magnetisation of the permanent magnets 113. This means that, as the rotor is deflected, for example in the distal direction (i.e. to the left), the magnetic attraction between the poles attempts to move the rotor back into the shown position. Since the rotor, as it rotates, conveys blood from the inlet in the direction of the outlet, the pressure of the liquid attempts to push the rotor in the distal direction. The arrangement of the permanent magnets 112 and 113 prevents this.

The permanent magnets 112 and 113 can be formed as ring magnets. For example, the permanent magnets 112 can thus be cylinder bushings, the upper end of which forms one pole and the lower end of which forms the opposite pole of the magnet.

Upon rotation of the rotor, a blood flow is excited in the gap 114 between the proximal end of the spiral outlet, the mandrel, and the rotor, which blood flow acts as a hydrodynamic bearing. The blood pump 100 therefore does not comprise any active bearings, but instead merely passive bearings. In the present example the blading 109 of the rotor 107 does not have any magnetisation. However, in some exemplary embodiments it can be provided to arrange a ring (magnetised or un-magnetised) radially outside the blading, which ring is used as a damping member between an outer side of the ring and an inner side of the housing or the cylindrical cavity and/or as part of the axial, passive bearing. In a further embodiment the ring secured to the blading and surrounding same can be of such a size that a hydrodynamic bearing is formed between the ring and an inner wall of the inlet. Only from an accordingly small gap width do the bearing forces become predominant, i.e. this construction on its own can radially support the rotating rotor. In the case of larger gap widths, the supporting forces are insufficient, and further bearings, for example magnetic bearings, have to be provided in order to radially support the rotor.

A further blood pump 200 is shown in FIG. 5. This also comprises a distal inlet 201 and a proximal outlet 202. Compared to the start of the spiral chamber 203, the proximal outlet 202 has a widened cross-sectional area. The mandrel 204 corresponds substantially to the mandrel 104 of the blood pump 100. This is also true for the housing 205 and the stator arranged in the cavity 206. The rotor 207 differs from the rotor 107. The rotor 207 is also configured in such a way that the blading 208 is disposed merely in the distal portion 209, which lies distally of the proximal outlet 202. The proximal end 210 of the rotor is not provided with a blading. In order to set the rotor in rotation, the rotor comprises permanent magnets 211, which are disposed in the blading 208. Furthermore, the rotor 207 comprises axially magnetised permanent magnets 212, which in conjunction with the permanent magnets 213 of the mandrel 204, which likewise are axially magnetised, but in the opposite direction, form a passive magnetic axial bearing. In this exemplary embodiment as well, the liquid conveyed by means of the rotor attempts to push the rotor in the distal direction. The orientation of the permanent magnets 212 and 213 ensures that the rotor is held in its starting position. The blading of the blood pump disclosed in US 2010/0069847 A1 is considered to be an example of the blading of the blood pump 200. In contrast to the rotor presented in said document, the rotor according to this application shall have a cavity in its interior in order to be able to be fitted onto the mandrel. The embodiment of the blood pump of FIGS. 4 and 5 show fundamentally a cylindrical mandrel, on which a cylinder bushing shaped rotor is arranged, on the outer side of which there is, in turn, arranged a blading.

A different construction is selected in the case of the blood pump 300 of FIG. 6. The blood pump 300 comprises a distal inlet 301 and a proximal outlet 302. The proximal outlet 302, in contrast to the spiral chamber 303, has an enlarged cross-section. A mandrel 304 extends from the proximal end to the distal end and comprises an annular recess 305, in which a rotor 306 is arranged. The mandrel 304 can be constructed here for example from a distal portion 307 and a proximal portion 308, wherein the distal portion 307 reaches substantially as far as the annular recess 305. The distal portion 307 can only be screwed on for example when the rotor 306 has been inserted into the annular recess 305.

Stator components 309 and 310 are arranged in the mandrel 304 and can set the rotor in rotation. For this purpose, the rotor comprises permanent magnets 311, which are oriented in such a way that they can be acted on by the stator with a force. Furthermore, the blood pump 300 comprises further permanent magnets 312 and 313, which are oriented axially and in cooperation form a passive axial magnetic bearing. A gap 314 is provided in the radial direction between an inner side of the rotor and an outer side of the annular recess, in which gap a blood film can be formed as soon as the rotor has been set in motion. The gap thus forms a hydrodynamic plain bearing. Here, the rotor can be formed in such a way that the cylinder bushing shape reaches substantially radially as far as the radial extent of the mandrel outside the annular recess. Thus, only the blading 315 extends into the interior 318 extending between the housing inner wall 316 and the radial outer diameter 317 of the mandrel. Alternatively to the passive axial magnetic mounting, the gaps 319 and 320 can be dimensioned in such a way that they likewise form an axial hydrodynamic plain bearing. In this case, the permanent magnets 312 and 313 can be spared. Alternatively, the axial position of the rotor 306 can also be controlled by means of an active axial mounting. Since the blading 315 is arranged radially outside the recess, the fluid can be effectively conveyed in the gap 318.

Further embodiments are illustrated in FIGS. 7 and 8. The blood pump 400 comprises a distal inlet 401 and a proximal outlet 402. The proximal outlet 402 is connected to the spiral chamber 403 and in this exemplary embodiment has an enlarged crosssection. A mandrel 404, which comprises a distal portion 405 and a proximal portion 406, which are coupled to one another by means of a shoulder 407, extends from the proximal end to the distal end. The shoulder 407 can also be referred to as a step. The housing wall 408 of the blood pump 400 widens in the region of the rotor 409 from the distal inlet to the proximal outlet. Although the mandrel 404 is fundamentally cylinder-shaped, the radially outer circumference of the rotor has a radial widening 410. Compared to radial pumps, however, the widening is configured such that the greatest gradient of the widening lies at the distal end 411 of the rotor 409 and the smallest curvature of the rotor 409 lies at the proximal end 412. It can be clearly seen that the proximal end of the rotor bears against the shoulder 407. The outer circumference of the rotor 409 at the proximal end 412, without consideration of the blading 413, is substantially equal to the radial extent of the proximal portion 406 of the mandrel 404.

For example, the blading can be a spiral or another blading known from the prior art for VADs, as has been described for example in the exemplary embodiments of FIG. 4 or 5. The most distal point of the mandrel 404 is formed as the surface of a segment of a sphere. This is intended to improve the flow of blood around the mandrel.

In the proximal portion 406 of the mandrel 404, there is arranged a stator 414, which is configured in such a way that it interacts with the permanent magnet 415 of the rotor 409 and can thus set the rotor in rotation. The axial mounting can be provided for example by means of a combination of axially magnetised permanent magnets 416 and 417. In addition, the housing wall 408 in some exemplary embodiments acts as part of a hydrodynamic bearing in the axial direction. This is dependent substantially on the surface of the blading opposite the housing wall and the distance of the blading from the housing wall. If the rotor 409 moves in the distal direction, there is a risk that the blading 413 will contact the housing wall 408 in the distal direction. In particular in the case of a spiral as blading, it is to be assumed that the hydrodynamic forces between the spiral blading and the housing wall are insufficient to prevent contact. Thus, the permanent magnets 416 and 417 act as the sole axial mounting. Radial mounting is provided by the gap 418 between the mandrel 404 and the rotor 409. The same is true for the gap between the rotor 409 and the shoulder 407, which is fluidly connected to the gap 418.

The blading 413 extends over the entire length of the rotor, as considered from the distal end in the proximal direction.

FIG. 8 shows a blood pump 500, which corresponds substantially to the blood pump 400 of FIG. 7. The blood pump 500 also has a distal inlet 501 and a proximal outlet 502. A mandrel 504 with a shoulder 507 is also provided. In contrast to the exemplary embodiment of FIG. 7, the rotor 509 is not provided over its entire length with a blading 513. The blading 513 thus starts at a distance from the distal start of the rotor 509. In the exemplary embodiment of FIG. 8 as well, the rotor 509 is formed in such a way that the curvature of the radial outer surfaces decreases from the distal inlet to the proximal outlet. A stator 514 sets the rotor in rotation on the basis of permanent magnets. An axial mounting is also provided, which corresponds substantially to the axial mounting of FIG. 7. The mandrel 504 is flattened at its distal end. The rotor terminates flush with the end of the mandrel 504 arranged upstream.

Further exemplary embodiments will become clear to a person skilled in the art in an obvious manner.

The application, inter alia, also comprises the following aspects:

1. A blood pump (1; 100; 200; 300; 400; 500), preferably for assisting a heart, wherein the blood pump comprises a housing with an inlet (11; 101; 201; 301; 401) arranged upstream, an outlet (12; 102; 202; 302; 402) arranged downstream, and a mandrel (15; 104; 204; 304; 404; 504) arranged between the inlet and the outlet, and a rotor (18; 108; 208; 306; 409; 509) with an axis and blading (20; 109; 209; 315; 413; 513) is arranged on the mandrel coaxially and rotatably, wherein the rotor is magnetically mounted on the mandrel in an axial direction, wherein the outlet is arranged downstream of an end of the blading that is arranged downstream.
2. The blood pump according to aspect 1, wherein the outlet is arranged fully downstream of the end of the blading that is arranged downstream.
3. The blood pump according to either one of the preceding aspects, wherein the outlet defines an outlet direction that is inclined relative to the axis of the rotor by an angle of more than 45°, preferably between 80° and 100°.
4. The blood pump according to aspect 3, wherein the outlet comprises a volute (203; 303; 403).
5. The blood pump according to any one of the preceding aspects, wherein the rotor comprises a bushing and the blading is arranged along an outer circumference of the bushing.
6. The blood pump according to aspect 5, wherein the bushing and the mandrel are oriented relative to one another in such a way that a hydrodynamic bearing is formed between an inner circumference of the bushing and a surface of the mandrel.
7. The blood pump according to either one of aspects 5 or 6, wherein the bushing is a cylinder bushing.
8. The blood pump according to any one of aspects 5 to 7, wherein permanent magnets of an axial magnetic bearing are arranged in the bushing and in the mandrel.
9. The blood pump according to any one of aspects 5 to 7, wherein permanent magnets (112, 113; 212, 213; 312, 313; 416, 417) of an axial magnetic bearing are arranged in the bushing and in the housing.
10. The blood pump according to any one of the preceding aspects, wherein the blading comprises at least one spiral.
11. The blood pump according to any one of the preceding aspects, wherein a stator is provided for driving the rotor and the stator is arranged in the mandrel and/or in the housing, surrounding the rotor and/or proximally of the rotor.
12. The blood pump according to any one of the preceding aspects, wherein the mandrel is substantially cylindrical.
13. The blood pump according to any one of aspects 1 to 11, wherein the mandrel comprises a substantially annular recess (305), in which the rotor is rotatably mounted.
14. The blood pump according to aspect 13, wherein the blading is arranged radially outside the recess.
15. The blood pump according to any one of the preceding aspects, wherein the rotor is configured in such a way that the end of the blading that is arranged downstream is arranged further upstream than an end of the rotor that is arranged downstream.
16. The blood pump according to any one of the preceding aspects, wherein the mandrel comprises a first, distal portion (405) for receiving the rotor and a second portion (406), which is arranged proximally of the first portion, and, between the first and second portion, a shoulder (407) forms a stop for a proximal end of the rotor.
17. The blood pump according to aspect 16, wherein a diameter of the second portion is substantially equal to an outer diameter of the rotor without blading.
18. The blood pump according to any one of the preceding aspects, wherein the rotor is mounted hydrodynamically in the radial direction.

The invention claimed is:

1. A blood pump comprising:
   a housing having an inlet arranged upstream, and a transverse outlet arranged downstream;
   a mandrel arranged between the inlet and the outlet; and
   a rotor having an axis and including a blading arranged on the mandrel coaxially and rotatably, wherein the rotor is magnetically mounted on the mandrel in an axial direction, wherein the outlet is arranged fully downstream of an end of the blading that is arranged downstream,
   wherein the mandrel includes axial bearing magnets configured to interact with the rotor,
   wherein the mandrel comprises a first, distal portion for receiving the rotor and a second portion, which is arranged proximally to the first portion, and wherein, between the first and second portion, a shoulder forms a stop for a proximal end of the rotor.
2. The blood pump of claim 1, wherein the rotor comprises a bushing, and wherein the blading is arranged along an outer circumference of the bushing.
3. The blood pump of claim 2, wherein the bushing and the mandrel are oriented relative to one another in such a way that a hydrodynamic bearing is formed between an inner circumference of the bushing and a surface of the mandrel.
4. The blood pump of claim 2, wherein the bushing is a cylinder bushing.
5. The blood pump of claim 2, wherein permanent magnets of an axial magnetic bearing are arranged in the bushing and in the mandrel.
6. The blood pump according of claim 2, wherein permanent magnets of an axial magnetic bearing are arranged in the bushing and in the housing.
7. The blood pump of claim 1, wherein the blading comprises at least one spiral.
8. The blood pump of claim 1, wherein a stator is provided for driving the rotor and the stator is arranged in the mandrel, in the housing, or both, wherein the stator surrounds the rotor, is proximate to the rotor, or both.
9. The blood pump of claim 1, wherein the mandrel is substantially cylindrical.
10. The blood pump of claim 1, wherein the mandrel comprises a substantially annular recess in which the rotor is rotatably mounted.
11. The blood pump of claim 10, wherein the blading is arranged radially outside the recess.
12. The blood pump of claim 1, wherein the end of the blading that is arranged downstream is further upstream than an end of the rotor that is downstream.

13. The blood pump of claim 1, wherein a diameter of the second portion is substantially equal to an outer diameter of the rotor without blading.

14. The blood pump of claim 1, wherein the rotor is mounted hydrodynamically in a radial direction.

15. The blood pump of claim 1, wherein the blood pump is for assisting a heart.

16. The blood pump of claim 1, wherein the outlet defines an outlet direction that is inclined relative to the axis of the rotor by an angle between 80° and 100°.

17. The blood pump of claim 1, wherein the shoulder lies distally of the outlet.

\* \* \* \* \*